United States Patent
Liu et al.

[11] Patent Number: 5,597,632
[45] Date of Patent: Jan. 28, 1997

[54] SHEET FOR RETAINING FRESHNESS OF CUT FLOWERS

[76] Inventors: Bo Liu, 1-6-12, Higashi Naruocho, Nishinomiya-shi, Hyogo, Japan; Hideaki Suzuki, 2-7-1, Umami Kita, Koryo-cho, Kita Katsuragi-gun, Nara, Japan

[21] Appl. No.: 282,979

[22] Filed: Jul. 29, 1994

[30] Foreign Application Priority Data

Jul. 30, 1993 [JP] Japan ................ 5-042187 U

[51] Int. Cl.⁶ ........................................ A61F 13/02
[52] U.S. Cl. .............. 428/41.1; 428/219; 428/220; 428/317.1; 428/332; 428/333; 428/339; 428/340; 504/114
[58] Field of Search ................ 47/1.01; 427/4; 504/114; 428/328, 332, 339, 340, 352, 354, 40, 219, 220, 317.1, 333

[56] References Cited

U.S. PATENT DOCUMENTS

| | | | |
|---|---|---|---|
| 1,956,908 | 5/1934 | Neubert | 504/114 |
| 2,168,304 | 8/1939 | Meyer | 504/114 |
| 2,230,931 | 2/1941 | Bussert | 504/114 |
| 2,923,094 | 2/1960 | Ryan | 504/114 X |
| 4,167,832 | 9/1979 | Zetterquist et al. | 47/1 R |
| 5,102,715 | 4/1992 | Zetterquist | 428/137 |
| 5,135,771 | 8/1992 | Chackal | 427/4 |
| 5,201,925 | 4/1993 | Itzel et al. | 47/58 |
| 5,284,818 | 2/1994 | Shafer et al. | 504/115 |

FOREIGN PATENT DOCUMENTS

108601  4/1990  Japan .

*Primary Examiner*—Hoa T. Le

[57] ABSTRACT

The sheet for retaining freshness of cut flowers, which is used in water in a flower-vase, consists of a laminate of a substrate, a life-prolonging agent layer for cut flowers and a protective layer. The life-prolonging agent layer mainly comprises at least one aluminum compound and is substantially water-soluble. It is preferred that the life-prolonging agent layer substantially comprises no binder.

13 Claims, 1 Drawing Sheet

SHEET FOR RETAINING FRESHNESS OF CUT FLOWERS

FIELD OF THE INVENTION

The invention relates to a sheet for retaining freshness of cut flowers, which has an ability of retaining freshness of cut flowers by being placed into water fed to a vessel such as a flower vase for cut flowers.

BACKGROUND OF THE INVENTION

Various means for prolonging the life of cut flowers have been tried. For example the typical methods are as follows: 1) a flower is cut in water to improve water raising, 2) water is refreshed properly to avoid contact with rotten water and 3) the cut end of the stalk of a cut flower is burnt. However, in general, the methods of cutting a flower in water to improve water raising and of burning the cut end have very little effect and frequent refreshment of water is troublesome giving no high expectation of improving the life-prolonging effect.

On the other hand, a number of various chemicals called life-prolonging agents for cut flowers have been marketed from flower shops and gardening shops. Their life-prolonging effects and activities on cut flowers are different from each other. The main functions of the life-prolonging agent can be classified as (1) sterilization and prevention of growth of bacteria, (2) purification and clarification of water and (3) nutrition.

Chlorine-containing chemicals are used as the life-prolonging agents (1). Though such chlorine chemicals are excellent in sterilizing effect, most of them are volatile and thus exhausted in use and dispersed in air which cause them to lose their activities and to lose the life-prolonging effect on cut flowers. Therefore, a large quantity of the life-prolonging agent is required to maintain the effect. Also, chlorine chemicals may provide the potential for the formation of toxic chlorine gas. The quantities of chlorine-containing chemicals are inevitably restricted in order to prevent the chlorine odor. As a result, the chemical is eluted little by little for use. However, such a method has a disadvantage in that it cannot provide satisfactory life-prolonging effect. Such sterilizers include, for example, sodium dichloroisocyanurate, hypochlorites and chlorites.

As the life-prolonging agents (2), water-soluble inorganic aluminum compounds are generally used. They function to aggregate impurities and dust contained in water, to keep the water clear in which cut flowers are placed, to eliminate clogging of the ducts of the cut flowers with impurities, and to promote clear water raising to the stalks of the cut flowers. Because such a life-prolonging agent is generally odorless and nonvolatile, their effects are not eliminated as the time passes as seen in the aforementioned life-prolonging agents (1). However, the life-prolonging agents (2) are generally liquid and have a low pH and are difficult to handle. Such life-prolonging agents include, for example, polyaluminum chloride, aluminum sulfate, potassium alum and the like.

The nutritive agents (3) supply positive nutrients to cut flowers to aid the life-prolonging effect. However, they have substantially no effect on removing various bacteria and impurities present in water but rather tend to help bacteria proliferate. Further, since the nutritive agent alone has little life-prolonging effect on cut flowers, it is required to use it together with a sterilizing agent as described above. The nutritive agents are exemplified by glucose, sucrose, urea, potassium salts and the like.

Also as disclosed in U.S. Pat. No. 4,167,832, a sheet for keeping cut flowers fresh has been developed in which a life-prolonging agent layer containing chlorine sterilizers and so on is provided on one side of a substrate, while a pressure sensitive adhesive layer and a release liner are laminated on the other side of it. This sheet for keeping cut flowers fresh is used so that the release liner is peeled off and then the adhesive layer of the laminate of life-prolonging agent layer/substrate/pressure sensitive adhesive layer is wound on the stalk and is put into a vase as it is.

The surface layer of this sheet for keeping cut flowers fresh, i.e., the life-prolonging agent layer, contains a chlorine sterilizer and the chlorine sterilizing agent tends to contact with bare hands in many cases during treatment and thus it is detrimental to health. Also, when the sheet is placed in a vase together with cut flowers, almost all of the chlorine sterilizer is dissolved in water in a short period as it is exposed on the surface. When a large quantity of the chlorine sterilizer is dissolved out in such a way, chlorine odor floats in the surroundings which can badly affect the cut flowers. In addition, the chlorine sterilizer gradually loses its activity and therefore it becomes difficult to keep its life-prolonging effect for a long period when almost all of the sterilizer has been released in a short period after being placed in water. In order to offset such a fault of the sheet for keeping cut flowers fresh, U.S. Pat. No. 5,102,715 introduces a structure in which almost all parts of the periphery of the life-prolonging agent layer containing the chlorine sterilizer is covered with a water-impermeable layer and thus the chemical is dissolved out gradually through a specified part. However, this structure is also insufficient in the life-prolonging effect for cut flowers and a higher life-prolonging effect was sought.

The object of the invention is to provide a sheet for keeping cut flowers fresh which has a sufficient life-prolonging effect and can be easily handled and is very hygienic.

In order to select a life-prolonging agent optimum for the purpose, the life-prolonging effects of various life-prolonging agents for cut flowers mentioned above have been investigated. As the results, it was found that aluminum compounds, clarifiers for service water, have higher effect than other types of life-prolonging agents. Among them, aluminum sulfate was found to have an excellent life-prolonging effect on cut flowers.

As to aluminum sulfate, Japanese Laid-Open Patent Publication No. 108601 of 1990 proposes a method in which a substance prepared by adding a saccharide to aluminum sulfate is made as an aqueous solution or a powder and is placed into the water used for cut flowers.

However, aluminum sulfate is usually used in liquid form for use as a water-treating agent and requires troublesome handling. Furthermore, it is highly acidic and therefore tends to cause problems such as chemical damages by scattering. Even when used as powder, it is contacted by bare hands which is hygienically unfavorable. In any event, to use a liquid clarifier such as aluminum sulfate as a life-prolonging agent for cut flowers, the conventional methods have various difficulties in handling and hygiene and thus include difficulties in practical use at present.

SUMMARY OF THE INVENTION

We, the inventors, have investigated a method which provides the same effect as the method of placing an aluminum compound represented by liquid aluminum sulfate in water and can utilize the aluminum compound as a life-prolonging agent for cut flowers safely, hygienically and simply. It was found that, when it is used in a sheet form according to the invention, the same life-prolonging effect can be attained as when the liquid form aluminum sulfate is placed in water.

The sheet for retaining freshness of cut flowers according to the invention includes a life-prolonging agent layer for cut flowers formed on a substrate and a protective layer formed on the life-prolonging agent layer. The life-prolonging agent layer mainly comprises at least one aluminum compound and is substantially water-soluble.

As the substrate, it is preferable that it have a water permeability of 1000 $g/m^2 \cdot hr$ or lower, more preferably 100 to 500 $g/m^2 \cdot hr$. The most preferable substrate is a water-resistant paper having a wet tensile strength of at least 1.0 kg/15 mm.

The aluminum compounds used in the life-prolonging agent layer include aluminum sulfate, polyaluminum chloride, potassium alum and the like.

It is preferred for the life-prolonging agent layer to have a porosity of 5 to 95%, particularly 40 to 80%. Generally, the life-prolonging agent layer has a thickness of 5 to 500 microns.

The life-prolonging agent layer is preferred to comprise no binder essentially.

The protective layer may be a single layer such as a synthetic resin film, or a laminate of various layers or sheets. For example, the protective layer may be a laminate of pressure sensitive adhesive layer/protective sheet or a laminate of pressure sensitive adhesive layer/releasing layer, in which the adhesive layer is adhered to the life-prolonging agent layer.

Further, the protective layer may be a laminate of protective sheet (formed with two layers releasable therebetween)/pressure sensitive adhesive layer/release liner, in which the protective sheet is adhered to the life-prolonging agent layer. In this case, it is preferred that the release force between two layers of the protective sheet is larger than that between the adhesive layer and the release liner. The protective layer may be a laminate of first pressure sensitive adhesive layer/first release liner/second pressure sensitive adhesive layer/second release liner, in which the first pressure sensitive adhesive layer is adhered to the life-prolonging agent layer. The release force between the first pressure sensitive adhesive layer and the first release liner is preferably larger than that between the second pressure sensitive adhesive layer and the second release liner.

While the novel features of the invention are set forth particularly in the appended claims, the invention, both as to organization and content, will be better understood and appreciated, along with other objects and features thereof, from the following detailed description taken in conjunction with the drawings.

It will be recognized that some or all of the Figures are schematic representations for purposes of illustration and do not necessarily depict the actual relative sizes or locations of the elements shown.

DETAILED DESCRIPTION OF THE INVENTION

The fundamental constitution of the sheet for retaining freshness of cut flowers according to the invention is characterized by a life-prolonging agent layer 1 for cut flowers and a protective layer 3 which are provided successively on one side of a substrate 2. As this product has a fundamental structure in which the life-prolonging agent layer 1 is sandwiched between a substrate 2 and a protective layer 3, there is no chance of contacting the life-prolonging agent by bare hands. In addition, it can be easily handled, simply carried and is hygienic.

When the product of the invention is placed in the water, the life-prolonging agent layer 1 which is very water-soluble is dissolved in water in a short time, and the substrate 2 and the protective layer 3 which are bonded with the life-prolonging agent layer 1 are separated from each other in water. For example, when aluminum sulfate is used as the life-prolonging agent, the time required to completely dissolve the life-prolonging agent layer in water is shorter than about one hour. Accordingly, the substrate 2 and the protective layer 3 which are thereafter unnecessary in the water may be easily removed from the water. As a result, the product of the invention can be used so that a water-insoluble material is not present in a vase, thus not detracting from a good appearance. The effect of the life-prolonging agent is not changed by removing the substrate 2 and the protective layer 3.

As the life-prolonging agent, one may use water-soluble aluminum compounds such as aluminum sulfate, polyaluminum chloride and potassium alum. Among them, aluminum sulfate is preferred as it is particularly excellent in the freshness-retaining effect for cut flowers.

As the substrate 2, papers such as wood free paper, art paper, coated papers, cast coated paper, metal foil paper, kraft paper, polyethylene laminated paper and impregnated paper; water-insoluble sheets such as metal foil and synthetic papers; and synthetic resin films such as cellophane, flexible polyvinyl chloride, rigid polyvinyl chloride, polypropylene and polyethylene terephthalate can be used. Various printings may be applied to the surface of the substrate 2.

It is preferred to form the life-prolonging agent layer in the invention without a binder if possible. When an aqueous solution of the life-prolonging agent is directly coated on a substrate 2, some troubles may occur depending on the type of the substrate 2. For example, when aluminum sulfate is applied on a usual wood free paper surface, various problems are generated. Bubbles are formed and further the aqueous solution of aluminum sulfate oozes on the paper surface which fails to provide a satisfactory coating. Wrinkling and waving of paper are induced during drying to form an unsatisfactory product. It is believed that they are caused by the fact that the usual wood free paper has a high porosity and a low mechanical strength when wet with water. Also, it is feared that the paper (substrate 2) can be deteriorated (weakened) by a long-term storage or a storage under an atmosphere of high temperature and high humidity.

On the other hand, when an aqueous solution of aluminum sulfate is applied on the back of a coated paper such as an art paper of relatively low porosity, bubbles are formed on the front side to deteriorate the appearance and to interfere with the following printing disadvantageously. This undesirable effect is believed to be caused by the fact that part of the aqueous-solution of aluminum sulfate applied on the back side is oozed to the coated layer of the front side of the paper and calcium carbonate contained in the coated layer reacted with aluminum sulfate to generate carbon dioxide gas. Furthermore, when a synthetic resin film not substantially porous is used as the substrate 2, no sufficient adhesion can be attained as the smoothness of the film is high and the affinity between the synthetic resin film and the aqueous solution of aluminum sulfate is poor.

Under the environment mentioned above, we, the inventors, have investigated on a substrate 2 which can be easily coated by an aqueous solution of aluminum sulfate and can be printed on the surface and also is sufficient as a freshness-retaining sheet.

As a result, it has been found that, when a paper having a water permeability of 1000 g/m²·hr or lower, preferably 100 to 500 g/m²·hr was used as the substrate 2, the substrate has a preferred porosity range and is especially easily coated by an aqueous solution of aluminum sulfate. When the water permeability exceeded 1000 g/m²·hr, the substrate became excessively porous and aluminum sulfate (aqueous solution) oozed from the substrate surface to provide an unsatisfactory product. It is also believed that the substrate became wavy after drying which resulted in insufficient printing. Conversely, when the substrate is a synthetic resin film or the like having a water permeability of zero, it is difficult to form voids during the formation of the aluminum sulfate layer and curls are formed to make handling difficult perhaps because of high flatness of the surface.

The water permeability described above is a value calculated as follows. A transparent glass tube having a length of 150 mm, an inner diameter of 17 mm and a thickness of 2 mm open at both ends is prepared. A sample specimen to be tested (25 mm dia.) is adhered to one end of the glass tube with a water-impermeable adhesive [Scotch High Power Adhesive (Multipurpose) manufactured by Sumitomo 3M Co.] so that water is not leaked. Separately, a glass tube of the same specification as above was prepared and a water-impermeable PET film (Ester Film E5100, 50 µm manufactured by Toyobo Co.) is adhered to one end of the tube with the Scotch High Power Adhesive (Multipurpose) in the same manner as for the sample specimen mentioned above.

Then, each glass tubes are fixed in an air-conditioned chamber (20° C., 65% RH) so that their open ends were at the top and then 10 g of distilled water are fed from the tops of each glass tubes. The weights of each of the glass tubes are measured immediately after the feeding and after 5 hours. The quantity of water decreased is derived from the following equation as the water permeability T (g/m²·hr).

$T=[(A_0-A_1)-(B_o-B_1)]/5 \pi R^2$

R=Inner diameter of the glass tube (m)/2 (=0.0085 m).

$A_0$=Initial weight of the whole glass tube containing water set by the sample specimen ( time: 0) (g), $A_1$=Weight of the whole glass tube containing water set by the sample specimen after 5 hours (g), $B_0$=Initial weight of the whole glass tube containing water set by the PET film (time: 0) (g), $B_1$ =Weight of the whole glass tube containing water set by the PET film after 5 hours (g), and $B_0=B_1$ shows the quantity of water evaporated from the open top of the glass tube after 5 hours.

As the substrate 2 in the case of using aluminum sulfate as the life-prolonging agent, it is recommended to use a paper having a water permeability specified above for floatability. However, the coatability and the printability are further improved by using a paper having a specified wet tensile strength in addition to the specific water permeability. Also, when a substrate which retains its strength in water is used, it can be thought that the substrate is scarcely broken to contaminate the service water even if the freshness-retaining sheet is thrown in the service water and left for a long period.

When the freshness-retaining sheet for cut flowers according to the invention is used practically, it is cut to a size of approximately 3 cm×5 cm. Therefore, a considerable quantity of aluminum sulfate is required to get freshness-retaining effect by such a size. For the purpose, it is difficult to give a required quantity of aluminum sulfate layer by only one coating of the aqueous solution of aluminum sulfate on the substrate. Thus, a plural number of coatings (such as two or three times) are required inevitably. An aluminum sulfate layer having a proper porosity described below can be prepared by such a plural number of coating.

Further, if the wet strength of the substrate 2 to be coated by the aqueous solution of aluminum sulfate is low, web break tends to occur and it is likely that no sufficient coating (operation) can be given. Thus, we have investigated and have found that, when a water-resistant paper having a wet tensile strength of 1.0 kg/15 mm or higher, preferably 2.0 to 10 kg/15 mm in accordance with JIS-P8135 is used as the substrate 2, it is very stable during coating and excellent in the inhibition of paper breakage during drying, shows no troubles such as waving and wrinkling of the substrate after drying and has more improved printability to give a particularly preferred embodiment. Further, when such a substrate excellent in wet strength is used, it has been found that the paper quality is not deteriorated even when it is stored for a long period or under an atmosphere of high temperature and high humidity as a sheet containing aluminum sulfate.

In the case the wet strength is lower than 1.0 kg/15 mm, not only it is believed possible that paper breakage can occur during the preparation of the sheet for retaining freshness but also the periphery of the substrate becomes more easily breakable as the time passes during the use of the sheet and fine pulp fibers can float partly in water to contaminate water in the vase. As a result, it is believed possible that the cut face and the trachea of the cut flower may be clogged to decrease the life-prolonging effect of the cut flower. On the other hand, a paper having as high a water-resistance as 10 kg/15 mm or higher has a saturated effect and affects printability adversely and others in many cases and also is economically disadvantageous.

The methods for the preparation of a paper having a specified water-permeability and a paper having a specified wet tensile strength as mentioned above are not particularly restricted and they can be prepared by using natural pulps such as wood pulp and non-wood pulps such as hemp, bagasse, kenaf and bamboo and non-natural pulps such as rayon and synthetic pulps and by controlling their formulating ratio and the beating degree, the types and the quantities of internal additives, the types and the quantities of wet paper strength improvers or dry paper strength improvers added if required, and further the drying condition or the like when subjected to paper making.

In order to prepare a water-resistant paper having a specified wet tensile strength, in addition to the method of adding an internal paper strength improver as mentioned above, a method of applying various wet paper strength improvers by the on-machine size press coating process can be used. Of course, if required, a smoothening treatment by using a machine calender can also be used.

As the wet paper strength improver, a commercial product can be properly used and is not particularly restricted. Typical examples include resins containing epoxy groups such as polyamide-epichlorohydrin resins, polyamide-polyamine-epichlorohydrin resins and epoxidized polyamide resins as well as melamine-formaldehyde resins, urea-formaldehyde resins and polyethylene imine.

The dry paper strength improvers include, for example, polyacrylamide resins such as a salt or a quaternary ammonium salt of acrylamideaminomethylacrylamide copolymer, acrylamide-quaternary ammonium salt group-containing alkyl(meth)acrylate copolymer, and acrylamide-sodium acrylate copolymers, as well as raw starches, modified starches and vegetable gums.

The quantities of these wet and dry paper strength improvers is preferred to be controlled generally in the range of 0.2 to 1.5 weight % based on the absolutely dry pulp. Of course, the wet paper strength improver can be used in combination with the dry paper strength improver.

Of course, it is also possible to apply an aluminum sulfate solution on various substrates listed above. However, when they are merely applied, various difficulties occur as mentioned above and it is required to take some supplementary measures and processing means (such as provision of water-resistance and hydrophilic nature, roughening treatment, etc.) in order to avoid these difficulties. As a result, the process becomes complex and also the cost is increased and thus it is not necessarily practical. Therefore, as the substrate 2 of the present invention, a paper having a specified water-permeability which can be controlled easily during the paper-making process and also a water-resistant paper having a specified wet tensile strength are particularly preferred.

Next, the method for the application of the life-prolonging agent on a substrate 2 will be described by exemplifying a case using aluminum sulfate as the life-prolonging agent.

The existing state of aluminum sulfate is generally expressed by $Al_2(SO_4)_3 \cdot nH_2O$ and n is not constant. Therefore, the concentration and the applied quantity of aluminum sulfate are expressed by $Al_2(SO_4)_3$ basis (solid) in the present invention unless specified.

First, an aqueous aluminum sulfate solution (concentration: 5 to 30 weight %, viscosity: 2 to 30 cps, pH: 1 to 4) is prepared. This aqueous aluminum sulfate solution is applied on one side of a substrate and dried to form a film. In this case, to give a sufficient effect as the life-prolonging agent, the quantity of aluminum sulfate is preferably controlled within the range of 15 to 360 ppm, more preferably 30 to 180 ppm, as the effective concentration of aluminum sulfate when fed in water. A quantity less than 15 ppm can scarcely give a desired life-prolonging effect, while one of more than 360 ppm tends to cause chemical damage by the aluminum salt.

In general, the sheet for retaining freshness is used as a cut sheet of approximately 3 cm×5 cm (that is 15 $cm^2$). An average vase has a volume of about 1 liter. Therefore, it is supposed to be reasonable to use about 500 milliliters of water as the water for prolonging the life of cut flowers. Therefore, in order to feed a sheet for retaining freshness of 15 $cm^2$ in 500 milliliters of water to dissolve 15 ppm of aluminum sulfate, it is required to apply about 5 $g/m^2$ of aluminum sulfate per $m^2$ of the substrate. In order to dissolve 360 ppm, it is required to apply about 120 $g/m^2$ of aluminum sulfate.

As high an applying quantity as 120 $g/m^2$ cannot be attained by one application. It can be attained by multiple applications (usually twice). In this case, an air knife coater, a roll coater, a bar coater or a slot dye coater can be used preferably as the coater.

The sheet for retaining freshness has been found to solve various contradictory problems shown below in order to get the effect that a high amount of a life-prolonging agent is stably deposited on a substrate and the life-prolonging agent can be rapidly dissolved out when the sheet for retaining freshness is placed in water. We, the inventors, have repeated many trials by using various binders and by combining many thickeners to solve these problems.

Generally, it can be thought that the stable adhesion of a life-prolonging agent on a substrate is attained by using a large amount of binder for forming the life-prolonging agent layer. However, it is necessary to make the life-prolonging agent layer substantially water-soluble. Usual plastic binders such as SBR and acrylic resins are insoluble in water and cannot be used preferably. For example, when the plastic binder is comprised in the life-prolonging agent layer, the substrate is kept strongly combined to the protective layer by the life-prolonging agent layer so that it takes as long a period as several days or longer until the inner life-prolonging agent is substantially dissolved out and thus a rapid life-prolonging effect cannot be achieved such as that achieved by using a liquid life-prolonging agent.

Also, one might consider reducing the amount of the binder as far as possible or using a binder easily soluble in water such as starch and PVA and also using a thickener after the life-prolonging agent layer is formed to dissolve out the life-prolonging agent rapidly. However, if the amount of the binder is reduced, it can be assumed a stable adhesion of the life-prolonging agent on the substrate becomes difficult. When a binder easily soluble in water is used, the dissolved binder itself or the thickener is dissolved or dispersed in water and the tracheae of the cut flowers are clogged and the contamination of water in the vase is promoted unfavorably.

Furthermore, when a binder or a thickener as mentioned above is used, it tends to aggregate during the preparation of the coating solution by mixing with an aluminum sulfate solution or during coating. So, it is required to adjust finely the conditions such as concentration, temperature and pH during mixing and coating and it is very difficult to form a stable coating solution and to perform a satisfactory coating.

Thus, we have repeated the trials and have found that a life-prolonging agent layer satisfying the expected properties can be formed by thin coating an aluminum salt, which is an inorganic soluble crystal. The aluminum salt by common sense has no binding power by itself and thus it is believed that it can not form a layer and can not combine stably the substrate with the protective layer until the product is used.

The product in which the life-prolonging agent layer 1 is formed by using only life-prolonging agents without a binder is very useful. In this case, the life-prolonging agent layer 1 sandwiched between the substrate 2 and the protective layer 3 is dissolved very rapidly in water and the life-prolonging agent is released to water in a very short period. As a result, the substrate 2 and the protective layer 3 adhered with it are separated in water. For example, as aluminum sulfate constituting the life-prolonging agent is already released after one hour or shorter, the water contains only the aluminum sulfate containing absolutely no binder and a small amount of other nutrients mixed optionally in it in dissolved condition, after the substrate 2 and the protective layer 3 then unnecessary are removed from water. Thus, a water for cut flowers can be achieved in an absolutely same condition as in the case where a liquid life-prolonging agent is placed in water. Furthermore, when a commonly used transparent or opaque glass vase is used, it is of course preferable that the substrate 2 and the protective layer 3 which have become unnecessary can be removed from water.

A water-soluble aluminum salt satisfies the function of a layer combining stably the substrate 2 with the protective layer 3 before being placed in water by constituting the life-prolonging agent layer 1 with only a life-prolonging agent with no use of a binder. The reason this aluminum salt can be applied relatively stably, that is, in a thickness of 5 to 500 μm which can assure a high coating level to some extent is not very clear. However, one explanation is related to the fact that aluminum sulfate and potassium alum are crystals having water of crystallization. Thus, it can be considered that the force of hydrogen bond caused by the water of crystallization may constitute a part of the adhesive force between the molecules constituting the life-prolonging agent layer 1 and between the agent layer 1 and the substrate 2 as well as the protective layer 3. It was also assumed from the fact that, when the sheet for retaining freshness finally prepared is dried in a drying oven to remove all water contained in it, the layer is too deteriorated to constitute a layer and becomes fragile.

One reason why using polyaluminum chloride as the life-prolonging agent is successful is that a crosslinking reaction or hydrogen bond between the OH groups may constitute a part of the adhesive force of the life-prolonging agent layer 1 with the substrate 2 and the protective layer 3.

As the resultant sheet for retaining freshness is very thin, it is a simple but very important property in practice to cause no curl during its storage and transportation in order to be handled easily when it is adhered on cut flowers and their packages or placed in water for use. We, the inventors, have applied a life-prolonging agent layer 1 consisting of aluminum sulfate with substantially no binder by various methods and compared the resultant layers. As a result, it has been found that, though layers of various constitutions are formed depending on the aluminum sulfate concentration and the combination of application methods and drying conditions, undesirable curl is unlikely to be formed if pores are present in the life-prolonging agent layer 1. The presence of such pores can be found easily when the section parallel to the surface of the life-prolonging agent layer 1 is observed by an optical microscope at about 200 magnifications. However, when a porosity is made to be very high, it is required to thicken the life-prolonging agent layer 1 to assure the necessary coating amount. However, a too thick layer makes it difficult for the layer to keep its mechanical strength and the life-prolonging agent layer is broken at the center of the layer in the worst case.

In order to make it difficult for the layer to curl and to control the thickness of the life-prolonging agent layer 1 within the range of maintaining the mechanical strength, the porosity is preferably 5 to 95%, more preferably 40 to 80%. As one of the methods for the application satisfying the condition, the desired object can be accomplished by applying an aqueous aluminum sulfate solution on a substrate to a double layer (twice coating). Thus, though the reason is not clear, it has been found that a dense coated film is formed by the first coating and the layer once formed dense is destroyed by the second coating applied on it and a dried coated layer of aluminum sulfate having the desired porosity can be prepared also with a mild drying speed. In the case the porosity is lower than 5%, the aluminum sulfate layer absorbs the peripheral moisture to cause unfavorable curling of the substrate. Conversely, when it exceeds 95%, the binding power between the aluminum sulfate layers becomes weak and the aluminum sulfate layer (crystal) tends to lose the product value. Particularly at a porosity of 40 to 80%, a product having no tendency of curling and showing a sufficiently high binding power of the layer can be prepared.

As the conditions for controlling a preferred porosity as mentioned above, it is thought that various factors include the concentration of aluminum sulfate to be applied, the method for the application, the moisture content in the aluminum sulfate layer immediately after coating, the drying temperature, the degree of water absorption of the substrate to be coated and the surface condition may all have a complicated effect on porosity. Therefore, it is difficult to determine a condition absolutely at present. The upper limit of the thickness of the life-prolonging agent layer 1 has a high relationship to the porosity of it as mentioned above and it is observed that the life-prolonging agent layer 1 is broken into the substrate 2 and the protective layer 3 remaining its portion when the thickness reaches 1000 μm in the case where the porosity is within the range shown above causing no curl. It is because, when the thickness of the life-prolonging agent layer 1 containing substantially no binder and having substantially no adhesive power becomes too high, it becomes unable to function as a layer stably combining the substrate 2 with the protective layer 3. According to our trial, it is confirmed that a layer of up to 500 μm thick can function as such a layer and hence the upper limit of the thickness of the life-prolonging agent layer 1 is made to be 500 μm. In the case of 5 μm or less, the coating amount does not provide the desired life-prolonging effect.

Previously, a dense layer (having a porosity of zero) is practically prepared under a coating condition and its density is calculated. As the coated amount of the aluminum sulfate layer of the examples can be easily found from increase in weight of the coated life-prolonging agent layer after coating, the density of the life-prolonging agent layer is calculated from the measured thickness of the resultant layer. The porosity can be easily calculated from the ratio of it to the above density of the dense layer (having a porosity of zero). The porosities of each example described below were derived by the calculation. In the case the coated amount cannot be found, it can be calculated by a measurement by utilizing the insolubility of aluminum sulfate in ethanol as follows. In the measurement of porosity, some fluctuations are found due to the materials used and the measurements against the above calculated value. However, it can be sufficiently used as a simple method.

(1) A sheet of aluminum sulfate-coated paper (10 cm×10 cm) was prepared and its thickness is measured and the volume of the coated paper is calculated and defined to be $V0$.

(2) Then, the coated paper is cut to 100 pieces of 1 cm×1 cm and they are fed into a cylinder containing anhydrous ethanol full to the brim one by one. The volume of ethanol overflowed is measured and defined to be $V1$.

(3) The coated paper is taken out of ethanol and dried in air and then immersed in water for 1 hour to dissolve aluminum sulfate and then rinsed with water. Then, the substrate from which aluminum sulfate is removed is dried in air and its thickness is measured and the volume is calculated from its area of 100 cm$^2$ and defined to be $V0_1$.

(4) The substrate of 1 cm×1 cm prepared by the procedure (3) is measured by the method of (2) and the resultant volume of ethanol is defined to be $VI_1$.

From the above procedures (1) to (4), the porosity R (%) of the aluminum sulfate layer was derived by the following equation.

$$R=\{[(V0-V0_1)\times(V1-V1_1)]/(V0-V0_1)\}\times 100$$

As mentioned above, it is required that the life-prolonging agent layer 1 comprising aluminum sulfate is porous, but the other aluminum compounds such as aluminum polychloride and potassium alum gave no formation of remarkable curl even in the life-prolonging agent layer 1 in which no pore is observed at a glance. The reason is not clear but it is thought that the water of crystallization in aluminum sulfate is more unstable than that in other compounds.

As the life-prolonging agent, a mixture of the above aluminum compound such as aluminum sulfate with an additive such as urea, glucose and the like may be used. For example, the added amount of urea to an aqueous aluminum sulfate solution (concentration: 5 to 30 weight viscosity: 5 to 30 cps., pH: 1 to 4) is preferably 0.1 to 1 weight % and the added amount of glucose to the aqueous aluminum sulfate solution is preferably 1 to 10 weight %. Further, commonly used freshness retainers for cut flowers, such as germicides, e.g., 8-hydroxyquinoline sulfate and sodium dichloroisocyanurate; nutritive agents, e.g., sucrose; vegetable hormones, e.g., kinetin; and ethylene gas inhibitors, e.g., silver thiosulfate (STS) can be also used in combination with aluminum compounds. However, those easily forming toxic gas and of high odor should be avoided as much as possible.

The pH of water is lowered when an aluminum compound is dissolved in it. The pH is preferably controlled within the range of 3.5 to 5.5, more preferably 4.0 to 5.0. A pH lower than 3.5 gives a too high acidity and bad effects such as withering of leaves of cut flowers. A pH higher than 5.5 lowers the life-prolonging effect.

It is not necessary for the life-prolonging agent layer 1 to substantially comprise a binder. However, 10 weight % or less of a binder may be added to the layer if desired.

The protective layer 3 of the present invention is enough to have a function preventing the falling-off of the life-prolonging agent layer 1 for cut flowers and a direct contact of hand to the layer in handling the freshness-retaining sheet. It may consist of single layer or multiple layers.

The products shown in FIGS. 1 to 5 are prepared by placing the life-prolonging agent layer 1 for cut flowers between the substrate 2 and the protective layer 3. The protective layer 3 of the product of FIG. 1 consists of a synthetic resin layer and the product consisting of substrate 2/life-prolonging agent layer 1/protective layer 3 is placed in water as it is for use. The trade name and the method for use of the product can be printed on the substrate surface.

Figure 1:
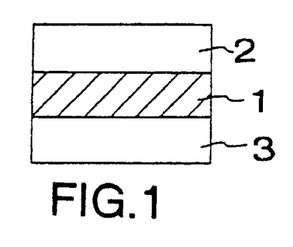
FIG. 1 is a sectional view of a sheet for retaining freshness of cut flowers according to the invention.

The protective layer 3 in FIG. 1 may consist of a single synthetic resin layer or multiple synthetic resin layers and the latter is generally preferred. The synthetic resins which can be used in the protective layer 3 include, for example, silicone resins such as polyether-modified silicones, epoxy-modified silicones, aminomodified silicones, carboxyl-modified silicones, carbinol-modified silicones, mercapto-modified silicones and higher fatty acid-modified silicones; polyolefin resins containing a reaction product of polymethyl hydrogen siloxane with polyolefin resin having double bonds; polyethylene resins; polypropylene resins; and polyester resins.

The laminating methods for the formation of a protective layer 3 by at least two synthetic resin layers include, for example, wet lamination, dry lamination, hot melt lamination, extrusion lamination and solvent lamination. Particularly, it is preferred to use extrusion lamination.

The protective layer 3 may be prepared by laminating on the back side of a synthetic resin layer a paper such as water-resistant paper, wood free paper, art paper, coated paper, metal foil paper or impregnated paper; a film such as polypropylene film or polyethylene terephthalate film; a metal foil or a laminated paper.

Figure 2:
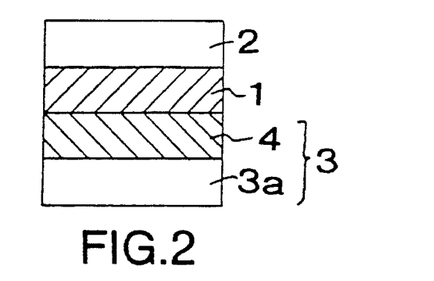
FIG. 2 is a sectional view of a sheet for retaining freshness of cut flowers according to the invention.

FIG. 2 shows a constitution in which the protective layer 3 is prepared by laminating a pressure sensitive adhesive layer 4 to a protective sheet 3a. The pressure sensitive adhesive layer 4 is contacted to the life-prolonging agent layer 1 for cut flowers. This product is also used by being placed in water in the same manner as the product shown in FIG. 1. In this case, as the protective sheet 3a, various sheets such as wood free papers, water-resistant papers, coated papers, nonwoven fabrics, synthetic resin films and metallized papers can be properly used.

Figure 3:
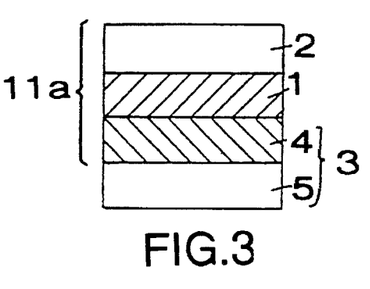
FIG. 3 is a sectional view of a sheet for retaining freshness of cut flowers according to the invention.

In FIG. 3, the protective layer 3 consists of a pressure sensitive adhesive layer 4 and a release liner 5. The pressure sensitive adhesive layer 4 is contacted to the life-prolonging agent layer 1 for cut flowers. The product is used by peeling the release liner 5 and placing the laminate 11a consisting of substrate 2/life-prolonging agent layer 1 for cut flowers/pressure sensitive adhesive layer 4 in water. The laminate 11a can be used by being wound around the stalk of the cut flowers with the pressure sensitive adhesive layer 4 and placed in water as it is.

Figure 4:
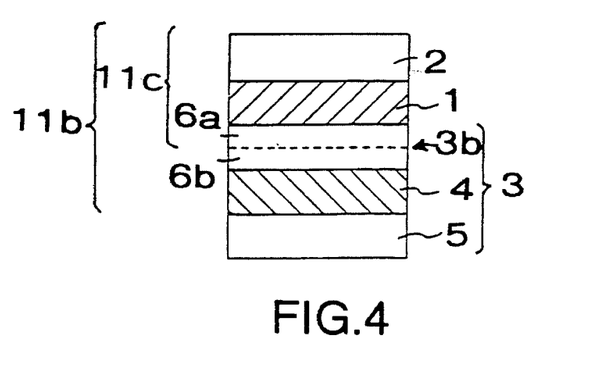
FIG. 4 is a sectional view of a sheet for retaining freshness of cut flowers according to the invention.

FIG. 4 shows an example in which the protective layer 3 consists of a protective sheet 3b consisting of two synthetic resin layers 6a, 6b, a pressure sensitive adhesive layer 4 and a release liner 5. The two sheets 6a and 6b constituting the protective sheet 3b are made to be peeled off from each other by a releasing agent or the like. This product is constituted so that the release liner 5 is peeled off and the laminate 11b consisting of substrate 2/life-prolonging agent layer 1 for cut flowers/protective sheet 3b/pressure sensitive adhesive layer 4 is adhered on the packaging paper of the bouquet with the pressure sensitive adhesive layer 4. When the bouquet is placed in a vase, the protective sheet 3b is peeled off between the two sheets 6a and 6b and the laminate 11c consisting of substrate 2/life-prolonging agent layer 1 for cut flowers/sheet 6a can be thrown in the water contained in a vase.

For such an application, it is preferred that the release force between the two sheets 6a and 6b constituting the protective sheet 3b is somewhat higher than that between the pressure sensitive adhesive layer 4 and the release liner 5. Usually, the former release force is preferably 10 to 800 g/50 mm, while the latter is 5 to 150 g/50 mm.

When the release force between the pressure sensitive adhesive layer 4 and the release liner 5 is lower than 5 g/50 mm, the release liner 5 is excessively easily peeled off from the product. Contrary to it, when it is higher than 150 g/50 mm, the release liner 5 cannot be easily peeled off from the pressure sensitive adhesive layer 4. Thus in both cases, it is difficult to handle. On the other hand, when the release force between the sheets 6a and 6b is lower than 10 g/50 mm, the two sheets 6a and 6b are easily peeled off from each other when the release liner 5 is peeled off, and resultantly the product cannot be adhered on a packaging paper or the like for cut flowers as a laminate 11b. When the release force exceeds 800 g/50 mm, the two sheets 6a and 6b cannot be easily peeled off from each other and the substrate 2 is broken during the peeling-off to make the product difficult to be handle.

The release force referred to here is a value of a force required for the peeling off of each adhered surface of a sample sheet of 50 mm wide at an angle of 180° and a peeling rate of 300 m/min. from the side of the substrate 2, which is expressed with a unit of g/50 mm.

Figure 5:
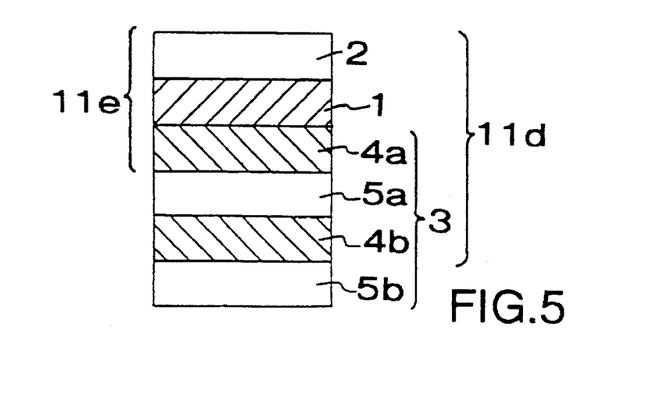
FIG. 5 is a sectional view of a sheet for retaining freshness of cut flowers according to the invention.

The product of FIG. 5 is a structure in which the protective layer 3 is a laminate consisting of first pressure sensitive adhesive layer 4a/first release liner 5a/second pressure sensitive adhesive layer 4b/second release liner 5b. The second release liner 5b is peeled off and the laminate 11d consisting of substrate 2/life-prolonging agent layer 1 for cut flowers/ first pressure sensitive adhesive layer 4a/first release liner 5a/second pressure sensitive adhesive layer 4b is adhered on a packaging paper or the like for cut flowers with the pressure sensitive adhesive layer 4b. The first release liner 5a is peeled off for use and the laminate 11e consisting of substrate 2/life-prolonging agent layer 1 for cut flowers/first pressure sensitive adhesive layer 4a is placed in water. On the relationship between the release force between the first pressure sensitive adhesive layer 4a and the first release liner 5a and that between the second pressure sensitive adhesive layer 4b and the second release liner 5b, the same thing can be said as in the relationship between the release force between the two sheets 6a and 6b constituting the protective sheet 3b and that between the pressure sensitive adhesive layer 4 and the release liner 5 in the product of FIG. 4.

In the present invention, various pressure sensitive adhesives such as acrylic type, rubber type, silicone type, vinyl ether type or the like can be used in the pressure sensitive adhesive layers 4, 4a and 4b. The pressure sensitive adhesives may be emulsion type, solvent type or nonsolvent type. It is preferred to use an acrylic emulsion adhesive from the cost consideration.

However, when aluminum sulfate is used in the life-prolonging agent layer 1 for cut flowers, it is preferred to use, in the pressure sensitive adhesive layers 4, 4a directly contacted with the life-prolonging agent layer 1, an acid-resistant adhesive, i.e., an adhesive of high barrier nature so that the highly water-absorptive acidic material does not pass through the pressure sensitive adhesive layers 4, 4a. As the acid-resistant adhesive, there are exemplified (1) Nissetsu KP-1230L manufactured by Nippon Carbide Industries Co., INC. as a solvent type adhesive and (2) Saibinol X-494-655E manufactured by Saiden Chemical Industries Co., Ltd. as a highly acid-resistant emulsion type adhesive prepared by using a nonionic surface active agent and by increasing the amount of a crosslinker. Particularly, a highly acid-resistant emulsion type adhesive is preferred economically as it can be used without solvent exhausting equipment.

The pressure sensitive adhesive layer can be usually formed by various coating processes. It can be formed by a coater such as a roll Crater, an air knife coater, a bar coater or a slot-die Crater. The pressure sensitive adhesive layer is preferably formed to about 5 to 50 g/m$^2$ on dry weight basis. A layer thinner than 5 g/m$^2$ has a weak adhesion and is not practical, while that thicker than 50 g/m$^2$ gives a saturated effect and is uneconomical.

Next, any commercial release liner can be used as the release liners 5, 5a and 5b. For example, the release liner may be prepared by coating a fluororesin, a silicone resin and the like in an amount of about 0.05 to 3 g/m$^2$ on dry basis on a high density base paper, a clay-coated paper, a kraft paper or a laminated paper prepared by laminating a resin such as polyethylene on a wood free paper, and then curing the resin thermally or by ionized radioactive ray to provide a releasing layer.

The outline of the preparation of the products shown in FIGS. 1 to 5 with use of aluminum sulfate in the life-prolonging agent layer 1 for cut flowers is described as follows.

The product shown in FIG. 1 is prepared by a procedure in which an aqueous aluminum sulfate solution of a defined concentration is applied on a surface of the substrate 2 and dried to form a lifeprolonging agent layer 1 for cut flowers and then the surface of said life-prolonging agent layer 1 for cut flowers is laminated with a synthetic resin such as polyethylene by an extrusion laminating method. While the extrusion laminating method is carried out to form a protective layer 3, corona is discharge is made on the surface of the life-prolonging agent layer.

The product shown in FIG. 2 is prepared by a procedure in which a life-prolonging agent layer 1 for cut flowers is formed on the surface of the substrate 2 in the same manner as for the product of FIG. 1. On the other hand, a pressure sensitive adhesive, preferably an acid-resistant adhesive is applied on a paper or the like (protective layer 3a) to form a pressure sensitive adhesive layer 4 and dried. The above life-prolonging agent layer 1 for cut flowers is adhered with the pressure sensitive adhesive layer 4 formed on the protective layer 3a.

The product shown in FIG. 3 is prepared by a procedure in which a life-prolonging agent layer 1 for cut flowers is formed on the surface of the substrate 2 in the same manner as for the product of FIG. 1. On the other hand, a pressure sensitive adhesive, preferably an acid-resistant adhesive is applied on the releasing surface of a release liner 5 to form a pressure sensitive adhesive layer 4 and dried. Then the above life-prolonging agent layer 1 for cut flowers is adhered with the pressure sensitive adhesive layer 4 formed on the release liner 5.

The product shown in FIG. 4 is prepared by a procedure in which a releasing paper prepared by applying a releasing agent on a support is used as the sheet 6b constituting a part of the protective sheet 3b and the releasing surface of the sheet 6b is adhered to a life-prolonging agent layer 1 for cut flowers provided on the surface of a substrate 2 with a sheet 6a (made of synthetic resin or the like) and then a release liner 5 having a pressure sensitive adhesive layer 4 is adhered on the sheet 6b with the pressure sensitive adhesive layer 4. The sheets 6a and 6b may be formed by a procedure in which the sheet 6a is formed in the same manner as for the protective layer 3 in FIG. 1 and the sheet 6b consisting of a synthetic resin is laminated to it by extrusion lamination while corona discharged. Alternately, a resin film or a paper or the like may be pressure-adhered as the sheet 6b when the sheet 6a is laminated.

The product shown in FIG. 5 is prepared by a procedure in which a pressure sensitive adhesive is applied on a release liner 5b to form a pressure sensitive adhesive layer 4b and dried and then the pressure sensitive adhesive layer 4b is adhered on the back side of the release liner 5a of the product formed in the same manner as for the product of FIG. 3.

The products of the present invention are useful in the retention of freshness of all cut flowers. For example, roses, carnations, chrysanthemums, stocks, Turkish bellflowers and bouvardias.

PREFERRED EMBODIMENTS OF THE INVENTION

The following examples serve to illustrate the invention in more detail although the invention is not limited to the examples. Unless otherwise indicated, parts and % signify parts by weight and % by weight, respectively. Further, the amount of the used aluminum salts, pressure sensitive adhesives and the like is shown in a solid amount. The amount of aluminum sulfate, water of crystallization of which is not stable, is shown in a solid amount as Al2(SO4)3, but that of potassium alum, water of crystallization of which is stable, is shown in a solid amount as KAl (SO4)2·12H2O.

Water-resistant papers L–N, wood free papers A–B, coated paper A for printing, and synthetic paper A used in Examples are as follows: (Water-resistant paper L)

Aluminum hydroxide was added to a mixed pulp slurry consisting of 50 parts of NBKP (Canadian standard freeness=475 ml) and 50 parts of LBKP (Canadian standard freeness=500 ml) to a paper ash content of 15%. Then, 0.5% of a higher fatty acid type size (NS-815 manufactured by Kindai Chemical Co., Ltd.), 0.2% of a polyacrylamide type dry paper strength improver (PS-273 manufactured by Arakawa Chemical Industries, Ltd.), 0.15% of aluminum sulfate and 0.7% of a wet paper strength improver containing polyamide-polyamineepichlorohydrin resin (WS-570 manufactured by JAPAN PMC CORPORATION) were respectively added based on the absolutely dry pulp and then the pulp was fed to a Fourdrinier paper machine to prepare a water resistant paper having a weight of 100 g/m$^2$, a wet tensile strength of 3.5 kg/15 mm and a water permeability of 250 g/m$^2$·hr. (Water-resistant paper M)

Labelling paper manufactured by Hokuetsu Paper Mills, Ltd., having a weight of 80 g/m$^2$, a wet tensile strength of 3.0 kg/15 mm and a water permeability of 150 g/m$^2$·hr. (Water-resistant paper N)

Separating base paper manufactured by New Oji Paper Co., having a weight of 78 g/m$^2$, a wet tensile strength of 2.1 kg/15 mm and a water permeability of 450 g/m$^2$·hr. (Wood free paper A)

Wood free paper having a weight of 64 g/m$^2$, a wet tensile strength of 1.0 kg/15 mm and a water permeability of 700 g/m$^2$·hr. (Wood free paper B)

Wood free paper having a weight of 36 g/m$^2$, a wet tensile strength of 0.5 kg/15 mm and a water permeability of 1300 g/m$^2$·hr. (Coated paper A for printing use)

A commercial coated paper having a weight of 157 g/m$^2$, a wet tensile strength of 1.5 kg/15 mm and a water permeability of 50 g/m$^2$·hr.
(Synthetic paper A)

Yupo TPG 60 manufactured by Oji Synthetic Paper Co., Ltd., which has a weight of 60 g/m$^2$, a wet tensile strength of 8 kg/15 mm and a water permeability of 0 g/m$^2$·hr.

Releasing papers A to C used in Examples were produced by the following method.
(Releasing papers A to C)

15 parts of a commercial silicone (KS-830E manufactured by Shin-Etsu Chemical Co., Ltd., silicone content: 30%), 0.15 part of a platinum catalyst and 84.85 parts of toluol were mixed together to prepare a silicone solution. Then, the solution was coated on a glassine paper (70 g/m$^2$) by using a bar Crater to obtain three releasing papers A to C. The coated amount of silicone is follows:

Releasing paper A: 0.85 g/m$^2$
Releasing paper B.: 1.0 g/m$^2$
Releasing paper C: 1.5 g/m$^2$

EXAMPLE 1

In this example, a product as shown in FIG. 1 was prepared. The water-resistant paper M was used as the substrate 2 and a life-prolonging agent layer 1 was applied on one side of the substrate 2. The aqueous aluminum sulfate solution (concentration: 27%) was applied by using a bar coater to a dry coated amount of 13.5g/m$^2$ as the first coating and dried at 120° C. for 2 minutes. Then, it was coated by using a bar coater to a dry coated amount of 27 g/m$^2$ as the second coating and dried at 100° C. for 2 minutes.

A polyethylene resin (Showlex L182 manufactured by Showa Denko K.K.) was extrusion-laminated on the surface of the lifeprolonging agent layer 1 to form a protective layer 3 of 20 A m thick.

During lamination corona discharge is made on the surface of the life-prolonging agent layer 1.

EXAMPLE 2

In this example, a product as shown in FIG. 1 was prepared in the same manner as in Example 1 except that the water-resistant paper L was used instead of the water-resistant paper M.

EXAMPLE 3

In this example, a product as shown in FIG. 1 was prepared in the same manner as in Example 1 except that the water-resistant paper N was used instead of the water-resistant paper M.

EXAMPLE 4

In this example, a product as shown in FIG. 1 was prepared in the same manner as in Example 1 except that the coated paper A was used instead of the water-resistant paper M.

EXAMPLE 5

In this example, a product as shown in FIG. 1 was prepared in the same manner as in Example 1 except that the wood free paper A was used instead of the water-resistant paper M. The porosity of the life-prolonging agent layer 1 was 70%.

EXAMPLE 6

In this example, a product as shown in FIG. 1 was prepared in the same manner as in Example 1 except that the synthetic paper A was used instead of the water-resistant paper M.

EXAMPLE 7

In this example, a product as shown in FIG. 1 was prepared in the same manner as in Example 1 except that the wood free paper B was used instead of the water-resistant paper M.

EXAMPLE 8

In this example, a product as shown in FIG. 1 was prepared in the same manner as in Example 1 except that aluminum sulfate was applied on one side of the water-resistant paper M to a dry coated amount of 27 g/m$^2$ by using a bar coater only once and dried at 120° C. for 2 minutes to form a life-prolonging agent layer 1.

EXAMPLE 9

In this example, a product as shown in FIG. 1 was prepared in the same manner as in Example 1 except that aluminum sulfate was applied on one side of the water-resistant paper M to a dry coated amount of 13.5 g/m$^2$ by using a bar coater as the first coating and dried at 120° C. for 2 minutes and then was coated again by using a bar boater to a total dry coated amount of 27 g/m² and dried at 160° C. for 2 minutes to form a life-prolonging agent layer 1.

EXAMPLE 10

In this example, a product as shown in FIG. 4 was prepared. A life-prolonging agent layer 1 mainly comprising aluminum sulfate was formed on a surface of the water-resistant paper M used as the substrate 2 in the same manner as in Example 1. Then, while corona discharged to the life-prolonging agent layer 1, a polyethylene resin (Showlex L182 manufactured by Showa Denko K.K.) was extrusion laminated on the life-prolonging agent layer 1 to form a synthetic resin sheet 6a of 20 g m thick and simultaneously a sheet 6b having a releasing agent layer adhered to the sheet 6a to obtain a laminate of substrate 2/life-prolonging agent layer 1/sheet 6a/sheet 6b in the manner as contacting the releasing agent layer with the sheet 6a.

The above sheet 6b having a releasing agent layer was prepared by applying, on a surface of the wood free paper A, a 15% solution of an acryl/vinyl chloride/vinyl acetate resin (SP-31105ET releasing agent manufactured by Teikoku Printing Inks MFG, Co., Ltd.) in a ketone hydrocarbon solvent (D-002 solvent manufactured by Teikoku Printing Inks MFG, Co., Ltd.) with use of a gravure printing machine in a solid amount of 2 g/m².

On the other hand, an acrylate copolymer emulsion adhesive (Nikasol L-145 manufactured by Nippon Carbide Industries Co., Ltd.) was applied on the releasing surface of a commercial glassine releasing paper (70GS(3) manufactured by Honshu Paper Co., Ltd.) having a weight of 70 g/m² to a solid content of 25 g/m² and dried to form a pressure sensitive adhesive layer 4 and then the adhesive layer 4 was adhered to the sheet 6b of the above laminate to form a product consisting of a laminate of substrate 2/life-prolonging agent layer 1/sheet 6a/sheet 6b/pressure sensitive adhesive layer 4/release liner 5.

EXAMPLE 11

In this example, a product as shown in FIG. 2 was prepared. The water-resistant paper M was used as the substrate 2, and a lifeprolonging agent layer 1 consisting of aluminum sulfate was formed on the substrate 2 in the same manner as in Example 1. Separately, an acrylate copolymer emulsion adhesive (Nikasol L-145 manufactured by Nippon Carbide Industries Co., Ltd.) was applied on a water-resistant paper M used as a protective sheet 3a to a coated amount of 15 g/m² and then the both materials were adhered together so that the pressure sensitive adhesive layer 4 contacted with the lifeprolonging agent layer 1 to obtain a laminated product of substrate 2/life-prolonging agent layer 1/pressure sensitive adhesive layer 1 4/protective sheet 3a.

EXAMPLE 12

In this example, a product as shown in FIG. 3 was prepared. The water-resistant paper M was used as the substrate 2, and a lifeprolonging agent layer 1 consisting of aluminum sulfate was formed on the substrate 2 in the same manner as in Example 1. Separately, an acrylate copolymer emulsion acid-resistant adhesive (Saibinol X-494655E manufactured by Saiden Chemical Industries Co., Ltd.) was applied on a releasing paper A used as a release liner 5 to a coated amount of 25 g/m² and then both materials were adhered together so that the pressure sensitive adhesive layer 4 contacted with the above life-prolonging agent layer 1 to prepare a laminated product of substrate 2/life-prolonging agent layer 1/pressure sensitive adhesive layer 4/release liner 5. The adhesive power between the pressure sensitive adhesive layer 4 and the release liner 5 was 60 g/50 mm.

EXAMPLE 13

In this example, a product as shown in FIG. 3 was prepared. The water-resistant paper M was used as the substrate 2 and an aqueous aluminum sulfate solution was applied once on one side of it so that the coated amount after dried is 27 g/m² and drying at 120° C. for 2 minutes. Separately, an acrylate copolymer emulsion adhesive (Nikasol L-145 manufactured by Nippon Carbide Industries Co., INC.) was applied on a releasing paper B used as a release liner 5 to a coated amount of 25 g/m² and then both materials were adhered together so that the pressure sensitive adhesive layer 4 contacted with the above life-prolonging agent layer 1 to prepare a laminated product of substrate 2/life-prolonging agent layer 1/pressure sensitive adhesive layer 4/release liner 5. The adhesive powder between the pressure sensitive adhesive layer 4 and the release liner 5 was 50 g/50 mm.

EXAMPLE 14

In this example, a product as shown in FIG. 5 was prepared. In addition to the laminated product prepared in the same manner as in Example 12, separately an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Mills, Ltd.), as a release liner 5b to a coated amount of 25 g/m² on dry basis and dried to form a pressure sensitive adhesive layer 4b. The obtained adhesive layer 4b was adhered to the above laminated product to obtain such a product as shown in FIG. 5 consisting of a laminate of substrate 2/life-prolonging agent layer 1/pressure sensitive adhesive layer 4a/release liner 5a/pressure sensitive adhesive layer 4b/release liner 5b.

EXAMPLE 15

In this example, a product as shown in FIG. 5 was prepared. In addition to the laminated product prepared in the same manner as in Example 13, separately an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Mills, Ltd.), as a release liner 5b to a coated amount of 25 g/m² on dry basis and dried to form a pressure sensitive adhesive layer 4b. The adhesive layer 4b was adhered to the above laminated product to obtain such a product as shown in FIG. 5 consisting of a laminate of substrate 2/life-prolonging agent layer 1/pressure sensitive adhesive layer 4a/release liner 5a(releasing paper B)/pressure sensitive adhesive layer 4b/release liner 5b.

EXAMPLE 16

In this example, a product as shown in FIG. 5 was prepared. The water-resistant paper M was used as the substrate 2 and an aqueous solution comprising 27% aluminum sulfate and 0.2% urea was applied once on one side of it so that the coated amount after drying is 27.2 g/m²(aluminum sulfate: 27 g/m², urea: 0.2 g/m²) in the same manner as in Example 13 to prepare a life-prolonging agent layer 1 containing aluminum sulfate and urea. Separately, an acrylate copolymer emulsion adhesive (Nikasol L-145 manufactured by Nippon Carbide Industries Co., INC.) was applied on a releasing paper B. as a release liner 5a to a coated amount of 20 g/m² to form a pressure sensitive adhesive layer 4a and then the both materials were adhered together so that the adhesive layer 4a contacted with the above lifeprolonging agent layer 1. Furthermore, an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Co., Ltd.), as a release liner 5b to a coated amount of 25 g/m² on dry basis and dried to form a pressure sensitive adhesive layer 4b. The adhesive layer 4b was adhered to the above release liner 5a to obtain such a product as shown in FIG. 5 consisting of a laminate of substrate 2/life-prolonging agent layer 1/pressure sensitive adhesive layer 4a/release liner 5a (releasing paper B)/pressure sensitive adhesive layer 4b/release liner 5b.

EXAMPLE 17

In this example, a product as shown in FIG. 5 was prepared. The water-resistant paper M was used as the substrate 2 and an aqueous solution consisting of 27% aluminum sulfate and 5% glucose was applied on one side of it so that the coated amount after drying is 32 g/m² (aluminum sulfate: 27 g/m², glucose: 5 g/m²) in the same manner as in Example 13 to prepare a life-prolonging agent layer 1 containing aluminum sulfate and glucose. Separately, an acrylate copolymer emulsion adhesive (Nikasol L-145 manufactured by Nippon Carbide Industries Co., INC.) was applied on a releasing paper B. i.e., release liner 5a to a coated amount of 20 g/m² to form a pressure sensitive adhesive layer 4a and then the both materials were adhered together so that the adhesive layer 4a contacted with the above lifeprolonging agent layer 1. Furthermore, an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Co., Ltd.), as a release liner 5b to a coated amount of 25 g/m² on dry basis and dried to form a pressure sensitive adhesive layer 4b. The adhesive layer 4b was adhered to the above release liner 5a to obtain such a product as shown in FIG. 5 consisting of substrate 2/life-prolonging agent layer 1/pressure sensitive adhesive layer 4a/release liner 5a (releasing paper B)/pressure sensitive adhesive layer 4b/release liner 5b.

EXAMPLE 18

In this example a product as shown in FIG. 5 was prepared. The water-resistant paper M was used as the substrate 2 and an aqueous aluminum polychloride solution (concentration: 30%) was applied on one side of it by using a bar Coated so that the coated amount after dried is 30 g/m² and drying at 120° C. for 3 minutes. Separately, an acrylate copolymer emulsion adhesive (Nissetsu KP-1230L manufactured by Nippon Carbide Industries Co., INC.) was applied on a releasing paper C as a release liner 5a to a coated amount of 15 g/m² to form a pressure sensitive adhesive layer 4a and then both materials were adhered together so that the adhesive layer 4a contacted with the above life-prolonging agent layer 1 consisting of aluminum polychloride. Furthermore, an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Col, Ltd.) as a release liner 5b to a coated amount of 25 g/m² on dry basis and dried to form a pressure sensitive adhesive layer 4b. The adhesive layer 4b was adhered to the above release liner 5a to obtain such a product as shown in FIG. 5 consisting of substrate 2/lifeprolonging agent layer 1/pressure sensitive adhesive layer 4a/release liner 5a (releasing paper C)/pressure sensitive adhesive layer 4b/release liner 5b.

EXAMPLE 19

In this example, a product as shown in FIG. 5 was prepared. The water-resistant paper M was used as the substrate 2 and an aqueous potassium alum solution (concentration: 10%) was applied on one side of it by using a bar coater so that the coated amount after dried is 10 g/m² and drying at 120° C. for 5 minutes to form a lifeprolonging agent layer 1 consisting of potassium alum. Separately, an acrylate copolymer emulsion adhesive (Nikasol L-145 manufactured by Nippon Carbide Industries Co., INC.) was applied on a releasing paper C as a release liner 5a to a coated amount of 20 g/m² to form a pressure sensitive adhesive layer 4a and then the both materials were adhered together so that the adhesive layer 4a contacted with the above life-prolonging agent layer 1. Furthermore, an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Co., Ltd.) as a release liner 5b to a coated amount of 25 g/m² on dry basis and dried to form a pressure sensitive adhesive layer 4b. The adhesive layer 4b was adhered to the above release liner 5a to obtain such a product as shown in FIG. 5 consisting of substrate 2/life-prolonging agent layer 1/pressure sensitive adhesive layer 4a/release liner 5a (releasing paper C)/pressure sensitive adhesive layer 4b/release liner 5b.

EXAMPLE 20

In this example, a product as shown in FIG. 5 was prepared. The synthetic paper A was used as the substrate 2 and aluminum sulfate was applied on it in the same manner as in Example 8 to a coated amount of 13.5 g/m² to form a life-prolonging agent layer 1. The other layers were constituted in the same manner as in Example 18 to prepare a laminated product consisting of substrate 2/life-prolonging agent layer 1/pressure sensitive adhesive layer 4a/release liner 5a (releasing paper A)/pressure sensitive adhesive layer 4b/release liner 5b.

EXAMPLE 21

In this example, a product as shown in FIG. 5 was prepared. The synthetic paper A was used as the substrate 2 and a lifeprolonging agent layer 1 was formed with aluminum sulfate in the sate manner as in Example 20. Separately, an acrylate copolymer emulsion adhesive (Nikasol L-145 manufactured by Nippon Carbide Industries Co., INC.) was applied on a releasing paper A as a release liner 5a to a coated amount of 15 g/m² to form a pressure sensitive adhesive layer 4a and then the both materials were adhered together so that the adhesive layer 4a contacted with the above life-prolonging agent layer 1. Furthermore, an acrylate copolymer emulsion adhesive (Nikasol L-145 manufactured by Nippon Carbide Industries Co., INC.) was applied on the releasing surface of a commercial glassine releasing paper (70GS(3), manufactured by Honshu Paper Co., Ltd.)

as a release liner 5b to a coated amount of 25 g/m² on dry basis and dried to form a pressure sensitive adhesive layer 4b. The adhesive layer 4b was adhered to the above release liner 5a to obtain such a product as shown in FIG. 5 consisting of substrate 2/life-prolonging agent layer 1/pressure sensitive adhesive layer 4a/release liner 5a (releasing paper A)/pressure sensitive adhesive layer 4b/release liner 5b.

The properties of the products obtained in Examples 1 to 21 were examined by the following tests. The results are shown in Tables 1 and 2. Further, porosity of each life-prolonging agent layer 1 formed in the Examples and water permeability of each substrate 2 used in the Examples are shown in Table 2.

Test (1)—Life-prolonging effect of cut flowers—

Rose, spray carnation, chrysanthemum and bouvardia grown in a vinyl plastic hothouse were used as the cut flowers to be tested. The flowers of as same a grown condition as possible were cut and trimmed by scissors in water at an angle of 30° against the stalk and vie cut flowers of the same type and a sheet (30×50 mm) of the product prepared in Examples were fed in a 1 liter wide-mouth bottle containing 500 milliliters of tap water. The condition of the cut flower was observed every day and the number of days in which the flower can be enjoyed was defined to be the life of the cut flower.

As the testing sheet, the products obtained in Examples 1 to 9 and 11 were used as they are, but in the product of Example 10 the residual product 11c obtained by removing the laminate of sheet 6b/pressure sensitive adhesive layer 4/release liner 5 was used. In the products obtained in Examples 12 and 13 the residual product 11a obtained by removing the release liner 5 was used, and in the products of Examples 14 to 21 the residual product 11e obtained by removing the laminate of releasing sheet 5a/pressure sensitive adhesive layer 5b/release liner 5b was used.

Test (2)—Coating applicability of a life-prolonging agent—Coating applicability when the life-prolonging agent was applied to the substrate was evaluated according to the following criteria.

⊚: The life-prolonging agent layer contains no bubble and the aqueous solution of life-prolonging agent does not ooze to the substrate surface giving a stable life-prolonging agent layer.

○: Slight out-oozing and foaming of the aqueous solution of life-prolonging agent are observed.

Δ: High out-oozing and much foaming of the aqueous solution of life-prolonging agent are observed unfavorably.

Test (3)—Curl of the substrate coated with a life-prolonging agent—

The substrate after being coated with the life-prolonging agent was placed in a constant temperature chamber (20° C., 65% RH) for 24 hours and then the appearance was observed and evaluated according to the following criteria.

⊚: Flat and no curling.

○: Through curling is observed no special problem in use.

Δ: Highly curled so that it is hard to handle.

Test (4)—Stability of the life-prolonging agent layer—

The life-prolonging agent layer formed on the substrate was lightly rubbed and the break-off of the agent was observed.

⊚: No break-off.

○: Slight break-off.

Test (5)—Storability—

The -products prepared in the Examples were stored in a chamber of 30° C. and 80% RH for 2 months and then the oozing of life-prolonging agents to the substrate surface was observed.

⊚: No oozing.

○: Slightly oozing. Care must be taken in use.

Δ: Highly oozing. The skin can be roughened when attached by hand.

Test (6)—Stability of the substrate—

The testing sheet as used in the above test (1) was immersed in tap water for 14 days and then the water was stirred lightly. The breakage of the substrate and the release of fine fibers from the substrate were observed.

⊚: No change is observed.

○: Though no release of pulp is observed, the substrate can be broken.

Δ: The substrate is broken and the pulp is somewhat released.

Test (7)—Stability against peeling—

As to the products of Examples 10 and 12 to 21, which were used by removing a release liner and the like, the peeling power required to remove the release liner and the like was measured. The stability against peeling was evaluated by the relation between the initial peeling power (A) and the peeling power (b) after storing the product in a chamber at 30<<C and 80 & RH for 2 months.

⊚: $0.5\ A \leq B \leq 1.5\ A$

○: $0.2\ A \leq B < 0.5\ A$ or $1.5\ A < B \leq 2.5\ A$

TABLE 1

| | Life of cut flowers (days) | | | |
|---|---|---|---|---|
| | Rose | Chrysanthemum | Spray Carnation | Bouvardia |
| Examples | | | | |
| 1 | 8 | 20 | 17 | 9 |
| 2 | 8 | 20 | 17 | 9 |
| 3 | 8 | 20 | 17 | 9 |
| 4 | 8 | 20 | 17 | 9 |
| 5 | 8 | 20 | 17 | 9 |
| 6 | 8 | 20 | 17 | 9 |
| 7 | 7 | 18 | 16 | 8 |
| 8 | 8 | 20 | 17 | 9 |
| 9 | 8 | 20 | 17 | 9 |
| 10 | 8 | 20 | 17 | 9 |
| 11 | 8 | 20 | 17 | 9 |
| 12 | 8 | 20 | 17 | 9 |
| 13 | 8 | 20 | 17 | 9 |
| 14 | 8 | 20 | 17 | 9 |
| 15 | 8 | 20 | 17 | 9 |
| 16 | 7 | 21 | 15 | 8 |
| 17 | 9 | 18 | 14 | 8 |
| 18 | 5 | 14 | 12 | 6 |
| 19 | 6 | 15 | 13 | 7 |
| 20 | 7 | 16 | 14 | 7 |
| 21 | 7 | 17 | 14 | 7 |
| Comparative Example[1] | | | | |
| | 4 | 12 | 9 | 4 |

[1] In the comparative examples, tap water is only used without any agent or any sheet for retaining freshness of cut flowers.

TABLE 2

TEST RESULTS

| Examples | Coating Applicability | Curling Curling | Stability of agent layer | Storability | Storability of substrate | Stability against peeling | Water permeability of substrate (g/m²) | Porosity of agent layer(%) |
|---|---|---|---|---|---|---|---|---|
| 1 | ⊙ | ⊙ | ⊙ | ⊙ | ⊙ | — | 150 | 40 |
| 2 | ⊙ | ⊙ | ⊙ | ⊙ | ⊙ | — | 250 | 45 |
| 3 | ⊙ | ⊙ | ⊙ | ⊙ | ⊙ | — | 450 | 50 |
| 4 | ⊙ | ○ | ⊙ | ⊙ | ○ | — | 50 | 25 |
| 5 | ○ | ⊙ | ⊙ | ○ | ○ | — | 700 | 70 |
| 6 | ⊙ | △ | ⊙ | ⊙ | ⊙ | — | 0 | 8 |
| 7 | △ | ⊙ | ○ | △ | △ | — | 1300 | 85 |
| 8 | ⊙ | ○ | ⊙ | ⊙ | ⊙ | — | 150 | 10 |
| 9 | ⊙ | ⊙ | ○ | ⊙ | ⊙ | — | 150 | 85 |
| 10 | ⊙ | ⊙ | ⊙ | ⊙ | ⊙ | ⊙ | 150 | 40 |
| 11 | ⊙ | ⊙ | ⊙ | ⊙ | ⊙ | — | 150 | 40 |
| 12 | ⊙ | ⊙ | ⊙ | ⊙ | ⊙ | ⊙ | 150 | 40 |
| 13 | ⊙ | ○ | ⊙ | ⊙ | ⊙ | ○ | 150 | 10 |
| 14 | ⊙ | ⊙ | ⊙ | ⊙ | ⊙ | ⊙ | 150 | 40 |
| 15 | ⊙ | ○ | ⊙ | ⊙ | ⊙ | ○ | 150 | 10 |
| 16 | ⊙ | ○ | ⊙ | ⊙ | ⊙ | ○ | 150 | 10 |
| 17 | ⊙ | ○ | ⊙ | ⊙ | ⊙ | ○ | 150 | 10 |
| 18 | ⊙ | ⊙ | ⊙ | ⊙ | ⊙ | ⊙ | 150 | 5 |
| 19 | ⊙ | ⊙ | ⊙ | ⊙ | ⊙ | ○ | 150 | 8 |
| 20 | ⊙ | △ | ⊙ | ⊙ | ⊙ | ⊙ | 0 | 5 |
| 21 | ⊙ | △ | ⊙ | ⊙ | ⊙ | ○ | 0 | 5 |

(Evaluation)
As to Test (1)

It was found that all life-prolonging agents showed remarkable life-prolonging effect on all types of cut flowers tested here. Particularly, aluminum sulfate was found to be excellent. It was also found that the leaves could be kept green when urea was further added. It was found that a further addition of glucose was effective for the retention of flower action. It was confirmed by a separate test now shown here that the above tendencies were substantially the same as in the case of aluminum sulfate when urea and glucose were further added to the other life-prolonging agents such as aluminum polychloride and potassium alum.

As to Test (2)

It was found that a too higher water permeability of the substrate did not give good applicability as shown by Examples 5 and 7 in which a highly water-permeable wood free paper was used as the substrate.

As to Test (3)

It can be thought that very high tendency of curling in Examples 6, 20 and 21 was caused by considerably low porosity of their life-prolonging agent layers. This reason was thought to be caused by using a synthetic paper having a water permeability of zero as the substrate. It can be also thought that the curling tendency in Example 4 was caused by the relatively low porosity of the life-prolonging agent layer (25%) and it was also caused by using a paper of relatively low waterpermeability as the substrate. Also in Examples 8, 13, 15, 16 and 17, it can be considered that the curling is caused by insufficient porosities due to only one coating of aluminum sulfate layer.

As the result of the investigation on the relationship between the curling and the porosity, it is though that the pores decrease the curling by the following reasoning. It is generally said that aluminum sulfate contains weather of crystallization of 18 $H_2O$. However, according to our trial, immediately after an application, an aluminum sulfate layer containing water of crystallization of 8 to 16 $H_2O$ was obtained by calculation. When a sheet having an aluminum sulfate layer containing water crystallization of 18 $H_2O$ was used, it was found that the aluminum sulfate layer further absorbed water and the layer was swollen to cause curling. However, it was found that such a curling did not occur when the layer contained pores even though the layer contained the same amount of water of crystallization. The reason was not clear but it was found that, such a curling did not occur when the layer contained pores even the layer contained the same amount of water of crystallization. The reason was not clear but it was thought that the swelling of the layer was absorbed by pores and made mild to make the formation of curling difficult. We have found empirically that it was advantageous to apply one or more coatings in order to form a layer of effectively porosity.

Potassium polychloride showed substantially no tendency of curling even if the layer contained no pore perhaps because of having no water of crystallization and it gave a good layer by only one coating. On the other hand, in the case of potassium alum stably containing water of crystallization of 12 $H_2O$, a layer containing water of crystallization of 12 $H_2O$ no pore and showed substantially no curling perhaps because of it.

As to Test (4)

It can be thought that the poorer stabilities of the life-prolonging agent layers of Examples 7 and 9 were caused by their higher porosities than the other Examples.

As to Test (5)

It can be thought that the poorer storabilities of Examples 5 and 7 were caused by the higher water permeabilities of their substrates than the other Examples. It is thought to be caused by the fact that a too high water permeability makes water absorption of aluminum sulfate easy and, when once part of aluminum sulfate has absorbed water, aluminum sulfate therearound absorbs water in series.

As to Test (6)

It was found from Examples 4, 5 and 7 that, when the wet tensile strength of the substrate is lowered, the substrate was more easily decomposed in use. However, the life-prolonging effect showed substantially no difference when practically measured perhaps because the decomposition of the substrate was not promoted by mixing.

As to Test (7)

It can be thought that the poor stabilities against peeling of Examples 13, 15, 16, 17, 19 and 21 than the other Examples were caused by the oozing of the pressure sensitive adhesive layers during storage. Those used an acid-resistant emulsion showed no such oozing.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A sheet for retaining freshness of cut flowers, in which a life-prolonging agent layer is formed on a substrate with a water permeability between 50 and 1000 $g/m^2 \cdot hr$ and a synthetic resin protective layer is formed on said life-prolonging agent layer, said life-prolonging agent layer mainly containing at least one aluminum compound selected from the group consisting of aluminum sulfate, aluminum polychloride and potassium alum and being substantially water-soluble.

2. A sheet as defined in claim 1, wherein said aluminum compound is aluminum sulfate and is present in an amount of 5 to 120 $g/m^2$ of the substrate and said life-prolonging agent layer has a thickness of 5 to 500 µm and a porosity of 5 to 95%.

3. A sheet as defined in claim 1, wherein said substrate has a water permeability of 100 to 500 $g/m_2 \cdot hr$.

4. A sheet as defined in claim 1, wherein said life-prolonging agent layer has a porosity of 5 to 95%.

5. A sheet as defined in claim 5, wherein said life-prolonging agent layer has a porosity of 40 to 80%.

6. A sheet as defined in claim 1, wherein said life-prolonging agent layer has a thickness of 5 to 500 microns.

7. A sheet as defined in claim 1, wherein said protective layer is a laminate of a pressure sensitive adhesive layer and a protective sheet, and said adhesive layer is adhered to said life-prolonging agent layer.

8. A sheet as defined in claim 1, wherein said protective layer is a laminate of a pressure sensitive adhesive layer and a release liner, and said adhesive layer is adhered to said life-prolonging agent layer.

9. A sheet as defined in claim 1, wherein said protective layer is a laminate of protective sheet/pressure sensitive adhesive layer/release liner, said protective sheet is adhered to said life-prolonging agent layer, and Said protective sheet is formed by two layers, the release force between which is larger than that between said adhesive layer and said release liner.

10. A sheet as defined in claim 1, wherein said protective layer is a laminate of first pressure sensitive adhesive layer/first release liner/second pressure sensitive adhesive layer/second release liner, said first pressure sensitive adhesive layer is adhered to said life-prolonging agent layer, and the release force between said first pressure sensitive adhesive layer and first release liner is larger than that between said second pressure sensitive adhesive layer and said second release liner.

11. A sheet as defined in claim 1, wherein said substrate is a water-resistant paper having a wet tensile strength of at least 1.0 kg/15 mm.

12. A sheet as defined in claim 1, wherein said life-prolonging agent does not substantially comprise a binder.

13. A sheet as defined in claim 1, wherein said life-prolonging agent layer contains aluminum sulfate in an amount of between 5 $g/m_2$ to 120 $g/m^2$ of the substrate but substantially no binder, and said substrate has a water permeability of 100 to 500 $g/m_2 \cdot hr$.

* * * * *